(12) United States Patent
Li et al.

(10) Patent No.: US 12,290,594 B1
(45) Date of Patent: May 6, 2025

(54) BAMBOO CHARCOAL POWDER-BASED FALSE EYELASHES AND PREPARATION PROCESS THEREOF

(71) Applicant: Qingdao Futesen Plastic Technology Co., Ltd, Qingdao (CN)

(72) Inventors: Kexiu Li, Qingdao (CN); Zhaozhong Zhang, Qingdao (CN)

(73) Assignee: Qingdao Futesen Plastic Technology Co., Ltd, Qingdao (CN)

( * ) Notice: Subject to any disclaimer, the term of this patent is extended or adjusted under 35 U.S.C. 154(b) by 0 days.

(21) Appl. No.: 18/402,112

(22) Filed: Jan. 2, 2024

(30) Foreign Application Priority Data

Dec. 6, 2023 (CN) .......................... 202311663757.4

(51) Int. Cl.

| | |
|---|---|
| *A41G 5/02* | (2006.01) |
| *A01N 55/00* | (2006.01) |
| *A01N 65/44* | (2009.01) |
| *A61K 8/02* | (2006.01) |
| *A61K 8/58* | (2006.01) |
| *A61K 8/9794* | (2017.01) |
| *A61Q 1/00* | (2006.01) |
| *C08J 5/06* | (2006.01) |
| *C08K 3/04* | (2006.01) |
| *C08K 5/5419* | (2006.01) |

(52) U.S. Cl.
CPC ............ *A61K 8/9794* (2017.08); *A01N 55/00* (2013.01); *A01N 65/44* (2013.01); *A41G 5/02* (2013.01); *A61K 8/027* (2013.01); *A61K 8/585* (2013.01); *A61Q 1/00* (2013.01); *C08J 5/06* (2013.01); *C08K 3/04* (2013.01); *C08K 5/5419* (2013.01); *C08J 2331/06* (2013.01)

(58) Field of Classification Search
None
See application file for complete search history.

(56) References Cited

U.S. PATENT DOCUMENTS

2012/0183619 A1* 7/2012 Lellouche ............. C07F 7/1804
424/490
2022/0279883 A1* 9/2022 Lotti ..................... A41F 15/002

FOREIGN PATENT DOCUMENTS

CN 113355765 A * 9/2021

OTHER PUBLICATIONS

Definition of "based" from dictionary.com, accessed Jun. 4, 2024 (Year: 2021).*
Machine translation of CN-113355765-A, original document published Sep. 7, 2021 (Year: 2021).*
Standard sieves and mesh sizes from dellyod.50megs.com, accessed Feb. 2, 2016 (Year: 2016).*
Particle Size/Mesh Screen Comparison, from www.wovenwire.com, accessed Mar. 10, 2008 (Year: 2008).*
Li H, Bao H, Bok KX, Lee CY, Li B, Zin MT, Kang L. High durability and low toxicity antimicrobial coatings fabricated by quaternary ammonium silane copolymers. Biomaterials science. 2016;4(2):299-309. (Year: 2016).*
Dong F, Jia T, Wang Q, Liu Y, Ma L, Li S, Tang X, Feng S. Preparation of intrinsic antibacterial silicone rubber with matrix tethering quaternary ammonium salt groups. Materials Today Communications. Mar. 1, 2021;26:101695. (Year: 2021).*
Mousa M, Dong Y. Strong poly (vinyl alcohol)(PVA)/bamboo charcoal (BC) nanocomposite films with particle size effect. ACS sustainable chemistry & engineering. Jan. 2, 2018;6(1):467-79. (Year: 2018).*

* cited by examiner

*Primary Examiner* — Nissa M Westerberg

(57) ABSTRACT

A bamboo charcoal powder-based false eyelash is obtained by evenly mixing 90-96% of polyester particles, 3-8% of bamboo charcoal powder and 1-2% of adjuvant, subsequently hot melting, wire drawing and forming and then cooling. The false eyelash can be subjected to not only chemical sharpening tip but also physical sharpening tip, has greatly reduced weight and is environmental-friendly; an organosilicon quaternary ammonium salt structure and three chlorine atoms in the adjuvant synergistically take antibacterial effects, and a long carbon chain further enhances an antibacterial effect. The adjuvant promotes the dispersion of the bamboo charcoal powder which promotes the compatibility and combination of the adjuvant and a matrix resin, their combined action improves the antibacterial property of the false eyelashes, and therefore the prepared false eyelash has good antibacterial and anti-inflammatory effects, can well protect skins around eyes from being damaged by external environment, and has both aesthetics and high safety.

4 Claims, No Drawings

BAMBOO CHARCOAL POWDER-BASED FALSE EYELASHES AND PREPARATION PROCESS THEREOF

CROSS REFERENCE TO RELATED APPLICATIONS

This application claims foreign priority of Chinese Patent Application No. 202311663757.4, filed on Dec. 6, 2023 in the China National Intellectual Property Administration, the disclosures of all of which are hereby incorporated by reference.

TECHNICAL FIELD

The disclosure belongs to the technical field of cosmetics, and particularly relates to a bamboo charcoal powder-based false eyelash and a preparation process thereof.

BACKGROUND OF THE DISCLOSURE

Eyelashes grow on the front lip of the eyelid and have a protective effect, while false eyelashes are artificial eyelashes used to beautify eyes. Generally, by lengthening and thickening the eyelashes, the eyes look fuller and lively. The materials used to make false eyelashes include chemical fiber materials, hairs and the like. False eyelashes made from different materials exhibit different effects and safety.

There are little researches on the safety of false eyelashes in the existing technology. With the improvement of people's quality of life, the safety requirements for false eyelashes are more and more increasing. Bamboo charcoal powders contain rich minerals and various trace elements, so they have antibacterial and anti-inflammatory effects, can help protecting fragile skins around eyes if being used in false eyelashes. However, there are almost no researches on using bamboo charcoal powders in false eyelashes in the existing technology. Therefore, it is urgent to design a bamboo charcoal powder-based false eyelash, so that the false eyelashes can meet the needs of the public.

SUMMARY OF DISCLOSURE

The objective of the disclosure is to overcome the defects in the prior art and provide a bamboo charcoal powder-based false eyelash and a preparation process thereof.

The objective of the disclosure can be achieved by the following technical solution:

Provided is a bamboo charcoal powder-based false eyelash, comprising the following raw materials in percentage by mass: 90-96% of polyester particles, 3-8% of bamboo charcoal powder and 1-2% of adjuvant.

Further, the polyester particle is one of polyethylene terephthalate particles, polybutylene terephthalate particles and polyaryl ester particles.

Further, the bamboo charcoal powder is prepared by the following steps:

adding 2 g of bamboo charcoal and 200 mL of 65 wt % nitric acid into a 500 mL three-necked flask, heating to 80° C., refluxing and stirring for 6 h, cooling to room temperature after the reaction is ended, filtering and washing with deionized water until filtrate is neutral, and drying filter residue for 12 h at 110° C. to obtain the bamboo charcoal powder.

Further, the bamboo charcoal powder is in 25000 meshes.

Further, the adjuvant is prepared by the following steps:

S1, adding isocyanopropyl triethoxysilane, 3-chloro-1-propanol and N, N-dimethylamide into a three-necked flask under the protection of nitrogen at room temperature, adding triethylamine after evenly stirring, heating to 75° C. while stirring, sufficiently stirring at 75° C. to react for 3 h, cooling to room temperature after the reaction is ended, and distilling at reduced pressure to obtain intermediate 1. An amount ratio of isocyanopropyl triethoxy silane to 3-chloro-1-propanol to triethylamine to N, N-dimethylamide is 12.4 g: 5 mL; 3 mL; 50 mL.

The isocyanate group of isocyanate propyl triethoxysilane and the hydroxyl group of 3-chloro-1-propanol undergo addition reaction under the action of an organic amine catalyst triethylamine. The reaction process is as follows:

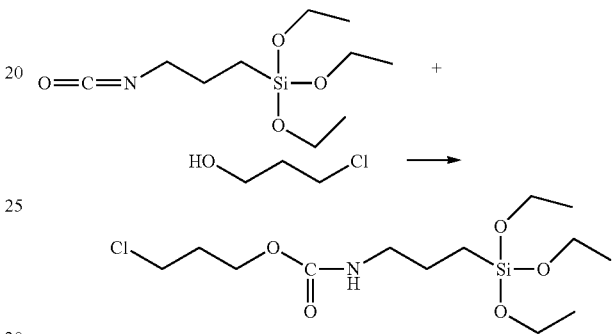

S2, adding the intermediate 1 and dimethyl sulfoxide into a four-necked flask under the protection of nitrogen at room temperature, sufficiently stirring until evenly mixing, subsequently heating to 40° C., then slowly adding tetradecyl dimethyl tertiary amine using a constant-pressure separating funnel, then heating to 50° C., stirring at 50° C. to react for 8 h, cooling to room temperature after the reaction is ended, distilling at reduced pressure to remove a majority of solvents, purifying via column chromatography (a mixed solvent of cyclohexane and ethyl acetate is selected as an eluent, and a volume ratio of cyclohexane to ethyl acetate is 8:2), and distilling at reduced pressure to remove the eluent to obtain intermediate 2. An amount ratio of intermediate 1 to tetradecyl dimethyl tertiary amine to dimethyl sulfoxide is 8.5 g: 8 mL; 50 mL.

—Cl in the intermediate 1 and tertiary amine in tetradecyl dimethyl tertiary amine undergo quaternization reaction under the heating condition to generate a quaternary ammonium salt. The reaction process is as follows:

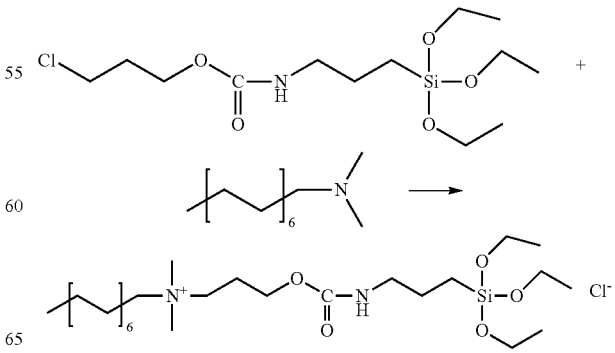

S3, adding the intermediate 2, triclosan and tetraisopropoxy titanium into a double-necked flask equipped with toluene, reacting for 24 h at 90° C., cooling to room temperature after the reaction is ended and then washing the reaction product twice with tartaric acid followed by washing three times with sodium bicarbonate, drying an organic phase using anhydrous magnesium sulfate, then filtering, distilling at reduced pressure, purifying via column chromatography (a mixed solvent of chloroform and diethyl ether is selected as an eluent, and a volume ratio of chloroform to diethyl ether is 9:1), and finally distilling at reduced pressure to remove the eluent to obtain the adjuvant. An amount ratio of intermediate 2 to triclosan to tetraisopropoxytitanium to toluene is 9.3 g: 4.6 g: 0.018 g: 60 mL.

The silane oxygen group in the intermediate 2 and hydroxyl in triclosan undergo the following chemical reaction under the action of a catalyst titanium tetraisopropoxy. The reaction process is as follows:

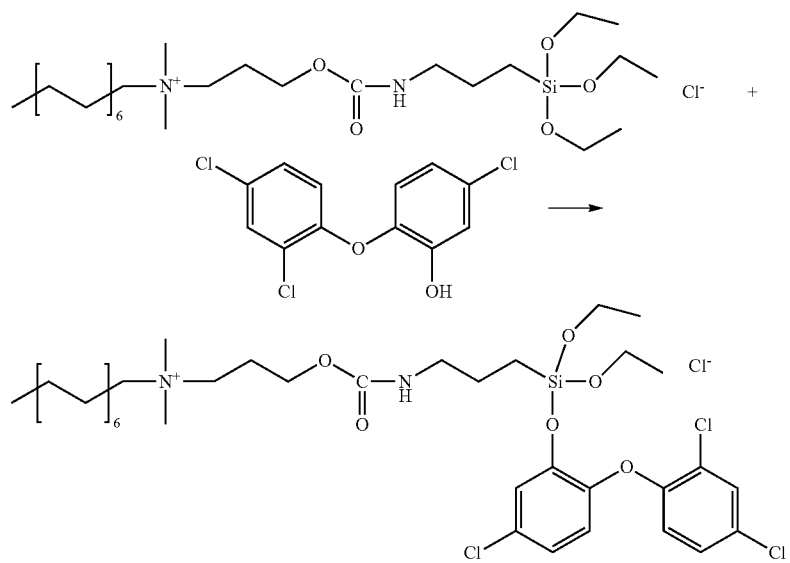

The adjuvant molecule contains an organosilicon quaternary ammonium salt structure which has good bactericidal effect on both *Staphylococcus aureus* and *Escherichia coli*. This is because cations in the organosilicon quaternary ammonium salt structure are adsorbed onto negatively charged bacteria through an electrostatic force and hydrogen bonds, and hydrophobic binding occurs between surfactants and proteins. The organosilicon quaternary ammonium salt causes the bacteria to produce a room resistance effect, and meanwhile the interaction between surfactant molecules and proteins changes the permeability of membranes in bacteria, so that the cell structure is changed, cell is ruptured, thereby leading to bacterial death; the antibacterial property of the quaternary ammonium salt is also related to the length of the alkyl chain of the quaternary ammonium salt, the antibacterial property of a quaternary ammonium salt antibacterial agent is the strongest when the number of carbon atoms in the alkyl chain of the quaternary ammonium salt is 14, and therefore the long carbon chain (14 carbons) enhances the antibacterial property of the adjuvant; the adjuvant molecule also contains three chlorine atoms which have strong oxidizing property and electron affinity, the chlorine atoms can react with a lipid molecule of their cell membrane when the adjuvant comes into contact with bacteria or fungi to cause the increase in damage and permeability of the cell membrane, which will cause imbalance in the internal and external environments of the cell and then fail to normally exchange important substances, hinder cell metabolism, and ultimately lead to bacterial and fungal death. The chlorine atoms work synergistically with the organosilicon quaternary ammonium salt to jointly improve the antibacterial property of the adjuvant; in the structure of the adjuvant, there is a silicon alkoxy group, which can form a chemical bond and a chemical force with the hydroxyl group on the surface of the bamboo charcoal powder, which will promote the high dispersion of the bamboo charcoal powder and enable the bamboo charcoal powder rich in minerals and various trace elements to take an antibacterial and anti-inflammatory effect. In addition, the bamboo charcoal powder treated by acid contains a large number of carboxyl and hydroxyl groups which can generate chemical forces with unreacted hydroxyl and carboxyl groups at the end of matrix particles, and therefore the bamboo charcoal powder also promotes the compatibility and combination of the adjuvant and the matrix particles, thereby enabling the adjuvant to take an antibacterial effect. In addition, the additive molecule also contains benzene rings, ester groups, amide groups and other functional groups, the adjuvant can be well compatible with the matrix particles due to similar compatibility, thereby fully and stably taking the antibacterial effect.

Provided is a preparation process of a bamboo charcoal powder-based false eyelash, comprising the following steps:
uniformly mixing raw materials in ratios, subsequently hot melting, wire drawing and forming, and cooling to obtain the bamboo charcoal powder-based false eyelash.

The disclosure has the beneficial effects: the false eyelash can be subjected to not only chemical sharpening tip but also physical sharpening tip, has greatly reduced weight and is environmental-friendly; the organosilicon quaternary ammonium salt structure and three chlorine atoms in the adjuvant synergistically take the antibacterial effect, and a long carbon chain (14 carbons) further enhances the antibacterial effect. The adjuvant promotes the dispersion of the bamboo charcoal powder which promotes the compatibility and combination of the adjuvant and a matrix resin, their combined action improves the antibacterial property of the false eyelashes, and therefore the prepared false eyelash has good antibacterial and anti-inflammatory effects, can well protect skins around eyes from being damaged by external environment, and has both aesthetics and high safety.

DETAILED DESCRIPTION OF PREFERRED EMBODIMENTS

Next, the technical solutions in embodiments of the disclosure will be clearly and completed described in combination with embodiments of the disclosure, obviously, the described embodiments are only some embodiments of the disclosure, but not all the embodiments. Based on the embodiments of the disclosure, other embodiments obtained by persons of ordinary skill in the art without creative efforts are all included within the scope of protection of the disclosure.

Example 1

An adjuvant was prepared by the following steps:
S1, 12.4 g of isocyanopropyl triethoxysilane, 5 mL of 3-chloro-1-propanol and 50 mL of N, N-dimethylamide were added into a 100 mL three-necked flask under the protection of nitrogen at room temperature, triethylamine was added after evenly stirring, the above materials were heated to 75° C. while stirring and sufficiently stirred at 75° C. to react for 3 h, and the reaction product was cooled to room temperature after the reaction was ended and distilled at reduced pressure to obtain intermediate 1;
S2, 8.5 g of intermediate 1 and 50 mL of dimethyl sulfoxide were added into a 100 mL four-necked flask under the protection of nitrogen at room temperature, sufficiently stirred until evenly mixing and subsequently heated to 40° C., then 8 mL of tetradecyl dimethyl tertiary amine was slowly added using a constant-pressure separating funnel, then the above materials were heated to 50° C. and stirred at 50° C. to react for 8 h, and the reaction product was cooled to room temperature after the reaction was ended, distilled at reduced pressure, purified via column chromatography (a mixed solvent of cyclohexane and ethyl acetate was selected as an eluent, and a volume ratio of cyclohexane to ethyl acetate was 8:2) and distilled at reduced pressure to obtain intermediate 2;
S3, 9.3 g of intermediate 2, 4.6 g of triclosan and 0.018 g of tetraisopropoxy titanium were added into a 100 mL double-necked flask equipped with 60 mL of toluene and reacted for 24 h at 90° C., and the reaction product was cooled to room temperature after the reaction was ended and washed twice with 5 wt % tartaric acid followed by washing three times with sodium bicarbonate, and an organic phase was dried using anhydrous magnesium sulfate, then filtered, distilled at reduced pressure, purified via column chromatography (a mixed solvent of chloroform and diethyl ether was selected as an eluent, and a volume ratio of chloroform to diethyl ether was 9:1), and finally distilled at reduced pressure to remove the eluent, so as to obtain the adjuvant.

Example 2

An adjuvant was prepared by the following steps:
The rest steps unchanged except that step S3 in example 1 was removed, so as to prepare the adjuvant.

Example 3

A bamboo charcoal powder was prepared by the following steps:
2 g of bamboo charcoal and 200 mL of 65 wt % nitric acid were added into a 500 mL three-necked flask, heated to 80° C., subjected to refluxing and stirring for 6 h, the above obtained mixture was cooled to room temperature after the refluxing and stirring was ended, filtered and washed with deionized water until filtrate was neutral, and filter residue was dried for 12 h at 110° C. to obtain the bamboo charcoal powder.

Example 4

A false eyelash was prepared by the following steps:
90% of polyarylester particles, 8% of bamboo charcoal powder in example 3 and 2% of adjuvant in example 1 were uniformly mixed, and subsequently the obtained mixture was subjected to hot melting, wire drawing and forming and cooled to obtain the bamboo charcoal powder-based false eyelash.

Example 5

A false eyelash was prepared by the following steps:
96% of polyethylene terephthalate particles, 3% of bamboo charcoal powder in example 3 and 1% of adjuvant in example 1 were uniformly mixed, and subsequently the obtained mixture was subjected to hot melting, wire drawing and forming and cooled to obtain the bamboo charcoal powder-based false eyelash.

Example 6

A false eyelash was prepared by the following steps:
94% of Polybutylene terephthalate particles, 4.5% of bamboo charcoal powder in example 3 and 1.5% of adjuvant in example 1 were uniformly mixed, and subsequently the obtained mixture was subjected to hot melting, wire drawing and forming and cooled to obtain the bamboo charcoal powder-based false eyelash.

Comparative Example 1

A false eyelash was prepared by the following steps:
The rest steps unchanged except that the adjuvant in example 6 was replaced with the adjuvant in example 2, so as to prepare the bamboo charcoal powder-based false eyelash.

Comparative Example 2

95% of polybutylene terephthalate particles and 5% of bamboo charcoal powder in example 3 were uniformly mixed, and subsequently the obtained mixture was subjected to hot melting, wire drawing and forming and cooled to obtain the bamboo charcoal powder-based false eyelash.

An antibacterial property test was performed on the adjuvant in example 1. The test results are seen in Table below:

| Test microorganisms | Amount of adjuvant | Number | Average colony count of positive control group | Total colony of test group | Antibacterial ratio % |
| --- | --- | --- | --- | --- | --- |
| Staphylococcus aureus | 1% | 1 | $1.4 \times 10^7$ | <10 | 99.99 |
| Escherichia coli | | 2 | $4.6 \times 10^7$ | <10 | 99.99 |
| Staphylococcus aureus | 1.5% | 1 | $1.4 \times 10^7$ | <10 | 99.99 |
| Escherichia coli | | 2 | $4.6 \times 10^7$ | <10 | 99.99 |
| Staphylococcus aureus | 2% | 1 | $1.4 \times 10^7$ | <10 | 99.99 |
| Escherichia coli | | 2 | $4.6 \times 10^7$ | <10 | 99.99 |

From the above data in Table, it can be seen that the adjuvants prepared in examples of the disclosure have excellent antibacterial effects. Therefore, the adjuvant of the disclosure and the bamboo charcoal powder can synergistically take antibacterial effects when used on false eyelashes, thereby greatly improving the antibacterial and anti-inflammatory effects of false eyelashes and allowing the false eyelashes to more safely and reassuringly use, so that the false eyelashes can meet the needs of the public in terms of safety and aesthetics. In the description of the specification, reference terms "one embodiment", "example", "specific example" and the like refer to a fact that specific features, structures, materials or characteristics described in conjunction with this embodiment or example are included in at least one embodiment or example of the disclosure. In the present specification, the illustrative expressions of the above terms may not necessarily refer to the same embodiments or examples. Moreover, the specific features, structures, materials or characteristics described can be appropriately combined in any one or more embodiments or examples.

The above contents are only examples and explanations of the disclosure. Those skilled in the art make various modifications or supplements of the described specific embodiments, or make replacement using a similar mode, as long as they do not deviate from the invention or go beyond the scope defined in the present claims, they should all fall within the scope of protection of the disclosure.

We claim:

1. A false eyelash, comprising the following raw materials in percentage by mass: 90-96% of polyester matrix made by polyester particles, 3-8% of bamboo charcoal powder and 1-2% of adjuvant;
wherein the adjuvant is represented by

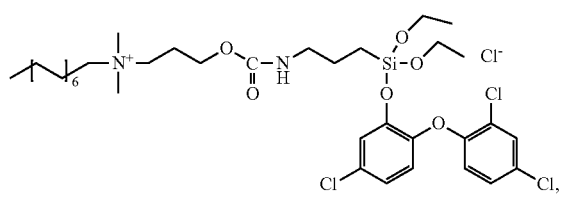

and the adjuvant is prepared by the following steps:
S1, adding isocyanopropyl triethoxysilane, 3-chloro-1-propanol and N,N-dimethylamide into a flask under the protection of nitrogen at room temperature, adding triethylamine after stirring, heating to 75° C., reacting for 3 h, cooling to room temperature, and then distilling at reduced pressure to obtain intermediate 1;

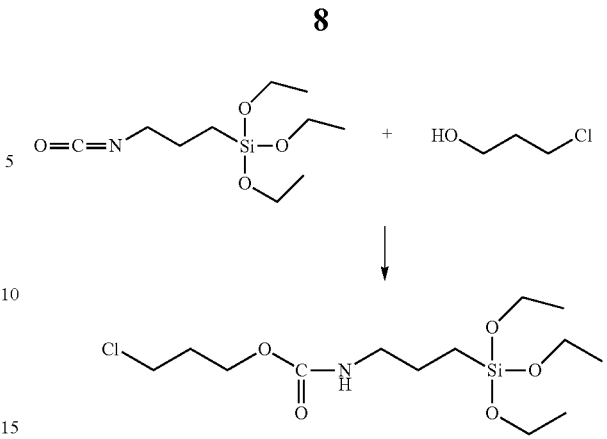

S2, adding the intermediate 1 and dimethyl sulfoxide into a flask under the protection of nitrogen at room temperature, stirring and heating to 40° C., then adding tetradecyl dimethyl tertiary amine, heating to 50° C. and reacting for 8 h, cooling to room temperature, distilling at reduced pressure, purifying via column chromatography, and then distilling at reduced pressure to obtain intermediate 2;

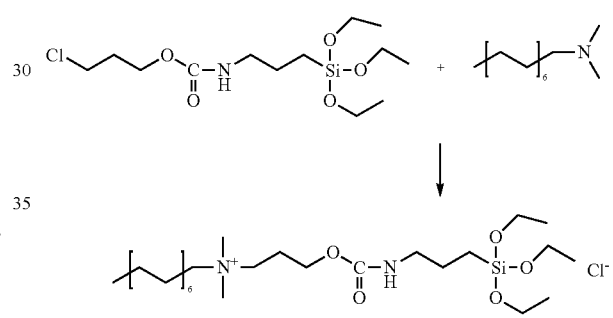

and

S3, adding the intermediate 2, triclosan and tetraisopropoxy titanium into a flask equipped with toluene, reacting for 24 h at 90° C., cooling to room temperature and then washing with tartaric acid followed by washing with sodium bicarbonate, drying, filtering, distilling at reduced pressure, purifying via column chromatography, and then distilling at reduced pressure to obtain the adjuvant

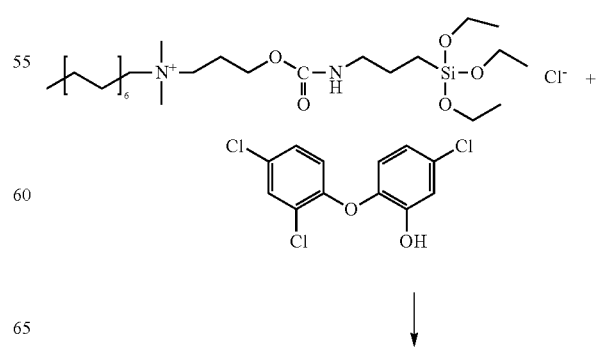

-continued

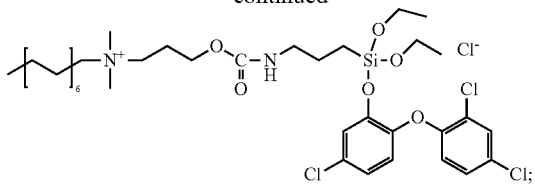

wherein an amount ratio of isocyanopropyl triethoxy silane to 3-chloro-1-propanol to triethylamine to N,N-dimethylamide in step S1 is 12.4 g: 5 mL: 3 mL: 50 mL;

an amount ratio of intermediate 1 to tetradecyl dimethyl tertiary amine to dimethyl sulfoxide in step S2 is 8.5 g: 8 mL: 50 mL;

an amount ratio of intermediate 2 to triclosan to tetraisopropoxytitanium to toluene in step S3 is 9.3 g: 4.6 g: 0.018 g: 60 mL.

2. The false eyelash according to claim 1, wherein the polyester particle is one of polyethylene terephthalate particles, polybutylene terephthalate particles and polyaryl ester particles.

3. The false eyelash according to claim 1, wherein the bamboo charcoal powder is prepared by the following steps:

adding 2 g of bamboo charcoal and 200 mL of nitric acid into a flask, heating to 80° C., refluxing and stirring for 6 h, cooling to room temperature, subsequently filtering, washing and drying to obtain the bamboo charcoal powder.

4. A preparation process of the false eyelash according to claim 1, comprising the following steps:

uniformly mixing the raw materials of claim 1, subsequently hot melting, wire drawing and forming, and cooling to obtain the false eyelash.

* * * * *